(12) United States Patent
Morikane

(10) Patent No.: US 6,206,902 B1
(45) Date of Patent: Mar. 27, 2001

(54) NOSE PACK

(75) Inventor: Daizo Morikane, Kashihara (JP)

(73) Assignee: Daiya Pharmaceutical Co., Ltd., Nara (JP)

( * ) Notice: Subject to any disclaimer, the term of this patent is extended or adjusted under 35 U.S.C. 154(b) by 0 days.

(21) Appl. No.: 09/088,716

(22) Filed: Jun. 2, 1998

(30) Foreign Application Priority Data

Feb. 6, 1998 (JP) .................................................. 10-824

(51) Int. Cl.$^7$ ........................................................ A61F 5/08
(52) U.S. Cl. ........................ 606/204.15; 602/41; 128/858
(58) Field of Search ................. 602/41, 61; 606/204.45; 2/606, 215, 174, 209; 128/858

(56) References Cited

U.S. PATENT DOCUMENTS 4,534,342 * 8/1985 Paxa .
5,512,277 * 4/1996 Uemura et al. .

* cited by examiner

Primary Examiner—Michael A. Brown
Assistant Examiner—Lalita Hamilton
(74) Attorney, Agent, or Firm—Breiner & Breiner

(57) ABSTRACT

A nose pack includes: a moisture-permeable base sheet, and a film-forming cosmetic substance contained in and carried by the base sheet; the base sheet having a slit in a lower portion thereof for defining an opening such that an upper edge of the opening is applicable to at least an apex portion of a nose.

19 Claims, 17 Drawing Sheets

NOSE PACK

BACKGROUND OF THE INVENTION

1. Field of the Invention

The present invention relates to improvements in a nose pack.

2. Description of the Prior Art

Nose packs are used to form a film on the nasal skin to absorb sebum on the skin, to impart the skin with tension, and to enhance the circulation of blood. By peeling off the pack from the skin later, it is possible to remove dirt, keratotic plugs and the like thereon and, hence, nose packs offer emollient and cleaning effects.

Peel-off type sheet packs have conventionally been used in terms of its ease in use. One such peel-off type nose pack is disclosed in, for example, Japanese Registered Utility Model Publication No 3034427. This nose pack comprises a carrier and a cosmetic substance and is so configured as to fit noses of various shapes.

It is an object of the present invention to provide a nose pack which is shaped different from conventional ones to fit even an apex portion of a nose and the periphery thereof easily, and is capable of forming a film in a shorter time and exhibiting a strong adhesion.

It is another object of the present invention to provide a nose pack which can be easily positioned on a nose bilaterally symmetrically in applying the pack on the nose.

It is a further object of the present invention to provide a nose pack capable of fitting undulating portions of a nose such as ala portions and groove portions at the outer edges thereof.

SUMMARY OF THE INVENTION

According to the present invention, there is provided a nose pack comprising a moisture-permeable base sheet and a film-forming cosmetic substance contained in and carried by the base sheet, the base sheet having a slit in a lower portion thereof for defining an opening such that an upper edge of the opening is applicable to at least an apex portion of a nose, or to the apex portion and at least adjacent peripheries of nostrils, or the apex portion, the adjacent peripheries of the nostrils and at least outer edges of ala portions.

With this construction, the slit formed in the nose pack: opens when a portion below the slit is pressed in applying the nose pack onto a nose. When the upper edge of the opening is pressed onto a nose, the nose pack sufficiently fits and covers, without strain, the apex portion, or the apex portion and at least the adjacent peripheries of the nostrils, or the apex portion, the adjacent peripheries of the nostrils and at least outer edges of the ala portions.

Further, the base sheet forms a film with a sufficient strength to prevent the nose pack from being torn upon peeling off.

Furthermore, the film thus formed can securely capture keratotic plugs and the like thereby reliably removes such keratotic plugs and the like when the pack is peeled off.

The foregoing and other objects, features and attendant advantages will become readily apparent from the reading of the following detailed description of the invention in conjunction with the attached drawings.

DETAILED DESCRIPTION OF THE PREFERRED EMBODIMENTS

Figure 1:
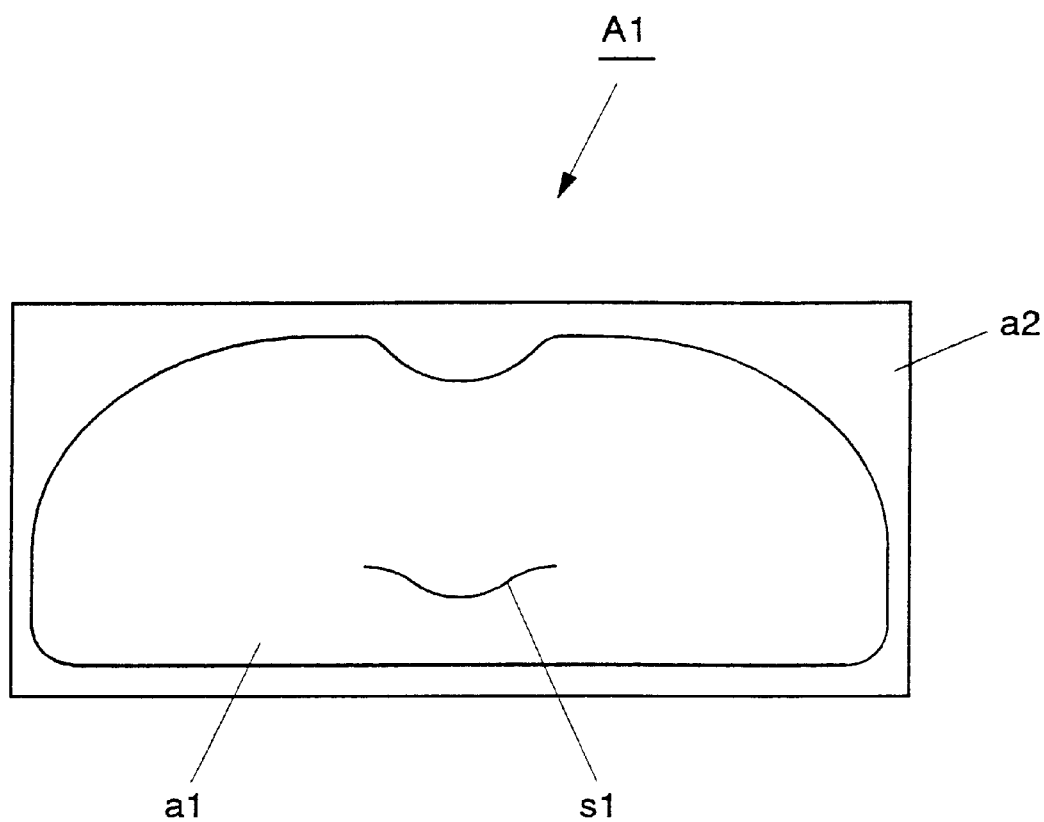
FIG. 1 is a plan view illustrating an example of the nose pack according to the present invention.

The present invention will now be described in detail with reference to the accompanying drawings.

In the present invention, the slit of the nose pack may be in the form of a single continuous line, or a broken line capable of forming a desired opening, or a slot having a small width.

Preferably, the slit is formed with at least one sub-slit extending upward therefrom so that the upper edge of the opening can be easily curved to fit the apex portion of a nose, peripheral portions of the nostrils, and outer edges of the ala portions.

It is also preferable that a vertically extending positioning slit is formed in a central portion of the moisture-permeable base sheet between the upper edge of the base sheet and the slit so that the nose pack can be easily applied onto the nose bilaterally symmetrically by aligning the positioning slit with the dorsum of the nose. It is to be noted that more than one positioning slit may be provided.

Instead of the positioning slit, a positioning hole may be provided in the base sheet. Such positioning hole reduces the rigidity of a center portion of the moisture-permeable base sheet, thereby making it easier to curve the nose pack.

Further, instead of the positioning means described above, a positioning mark (pp) comprising a raised mark, a depressed mark, or a combination thereof may be formed. Such a positioning mark is preferred because it does not reduce the strength of the moisture-permeable base sheet.

The positioning mark may be one formed by simply folding the basis sheet concavely or convexly.

The moisture-permeable base sheet according to the present invention may be in any form as long as it is capable of covering at least the dorsum portion, opposite ala portions and apex portion of a nose. For example, the moisture-permeable base sheet is shaped to have a central narrow portion by cutting away a central portion of the upper edge of the base sheet and a pair of arcuated wide portions formed on opposite sides of the narrow portion. Each wide portion has a sufficient area to cover each ala portion, while the cut-away central portion of the upper edge leaves the root portion of the nose as exposed even when the nose pack is applied onto the nose. However, the present invention is not limited thereto.

Preferably, each lateral edge portion of the moisture-permeable base sheet for covering each ala portion is formed with a plurality of small slits or notches extending inwardly from the lateral edge for easier curving.

Further, it is preferable that the portion for covering each ala portion is formed with slits so as to be bent conformally to the ala portion. In this case, the entire ala portion can be conformally covered by such portion so that the lateral edge portion can easily fit the periphery of the ala portion.

The moisture permeable base sheet may be formed of any conventionally known material in the art as long as it is water/moisture permeable but not detrimental to skin while being capable of containing and retaining a film-forming cosmetic substance therein. Examples of such materials include woven, non-woven, or knitted fabrics formed from natural fibers such as cotton, hemp, and wool; synthetic fibers such as nylon, vinylidene, polyvinylchloride, polyester, polyethylene, polypropylene, polyurethane and polyacrylate; cellulosic fibers such as rayon and acetate. Among these, those formed from hydrophobic fibers are preferably used.

The moisture-permeable base sheet preferably has a flexibility and stretchability so as to be readily conformable to the shape of a skin surface thereby providing enhanced adherence to the skin.

It is possible that the moisture-permeable base sheet comprises a foamed resin sheet having open cells.

If the moisture-permeable base sheet is formed from a fiber bland of a hydrophilic fiber and a water-repellent fiber, the amount of the firm-forming cosmetic substance contained in and carried by the base sheet can be advantageously controlled by varying the blending proportions of these fibers. Examples of the hydrophilic fibers include rayon and cotton, and examples of the water-repellent fibers include polyester fibers, polyolefin fibers, and nylon fibers, but the present invention is not limited thereto.

At least one of the hydrophilic fiber and the water-repellent fiber may be rendered hydrophilic and/or water-repellent by means of a surface-active agent.

The film-forming cosmetic substance in accordance with the present invention mainly comprises a film-forming material and a cosmetic material.

Typical examples of film-forming materials are those containing polyacrylic acid as a major ingredient thereof and. those containing polyacrylic acid and pullulan as major ingredients thereof.

In the former materials, polyacrylic acid is used in an amount of from 1 to 98% by weight (in a dry amount) based on, the total weight of the film-forming cosmetic substance. If it exceeds the upper limit, such properties as moisture retention, adhesion and comfortableness in use are undesirably degraded and, if it is less than the aforesaid lower limit, the film strength is insufficient.

In the latter materials, the total amount of polyacrylic: acid and pullulan to be used is from 1 to 98% by weight (in a dry amount) based on the total weight of the film-forming cosmetic substance. If it exceeds the upper limit, such properties as moisture retention, adhesion and comfortableness in use are undesirably degraded and, if it is less than the lower limit, the film strength is insufficient. The amount of pullulan to be used is preferably from 5 to 80% by weight relative to polyacrylic acids but not limited thereto.

The film-forming cosmetic substance may further contain a thickening agent as required. Examples of thickening agents include carboxymethylcellulose, pectin, gelatin, xanthan gum, sodium alginate, carboxyvinyl polymers and carrageenan.

The cosmetic material to be incorporated in the film-forming cosmetic substance includes conventionally known materials such as humectants and oil components.

Examples of such humectants include ethylene glycol and polyethylene glycols such as diethylene glycol and triethylene glycol; propylne glycol and polypropylene glycols such as dipropylene glycol and tripropylene glycol; butylene glycols; glycerin and polyglycerols such as diglycerol and the like; sugaralchols such as sorbitol, mannitol, xylitol, and maltitol; monosaccharides such as glucose, fructose and galactose; polysaccharides such as maltose and lactose, but the present invention is not limited thereto.

The oil component suitable for the present invention includes an oil component known as a so-called emollient component. Examples of such oil components include hydrocarbons such as squalane and liquid paraffin; natural oils such as olive oil, jojoba oil and coconut oil; esters such as isopropyl myristate and cetyl isooctanoate; silicone oil; higher fatty acids such as oleic acid and isostearic acid.

The film-forming cosmetic substance may further contain an astringent, a whitening component, an antiphlogistic, a colorant, a pigment, a surface-active agent, a microbicide and an antiseptic, as required.

The film-forming cosmetic substance of this invention is prepared to exhibit a fluidity in the presence of sufficient water and a film-formability under a dried condition.

EXAMPLE 1

FIG. 1 is a plan view of an example of a nose pack in accordance with the present invention. Nose pack (A1) shown comprises a moisture-permeable base sheet (a1), a film-forming cosmetic substance contained in and carried by the moisture-permeable base sheet (a1), and a release sheet (a2).

The base sheet (a1) is formed from a non-woven fabric of a polyester fiber material.

It is to be noted that the release sheet (a2) can be dispensed with as the case may be.

The nose pack (A1) has a configuration as shown in FIG. 1 in which a curved slit (s1) is formed in a lower portion of the moisture-permeable base sheet (a1).

The slit (s1) is in the form of a downwardly arcuated line and has a length substantially applicable to the apex portion of a nose.

Figure 2:
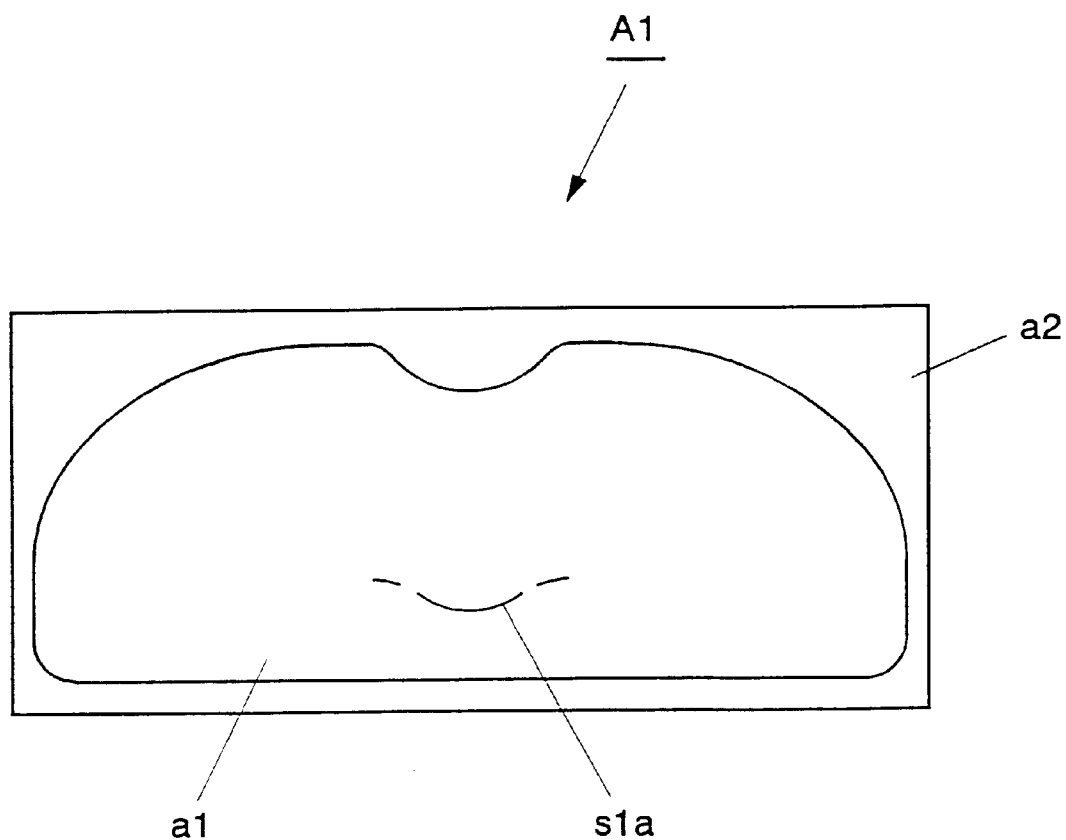
FIG. 2 is a plan view illustrating another example of the nose pack according to the present invention.
Figure 3:
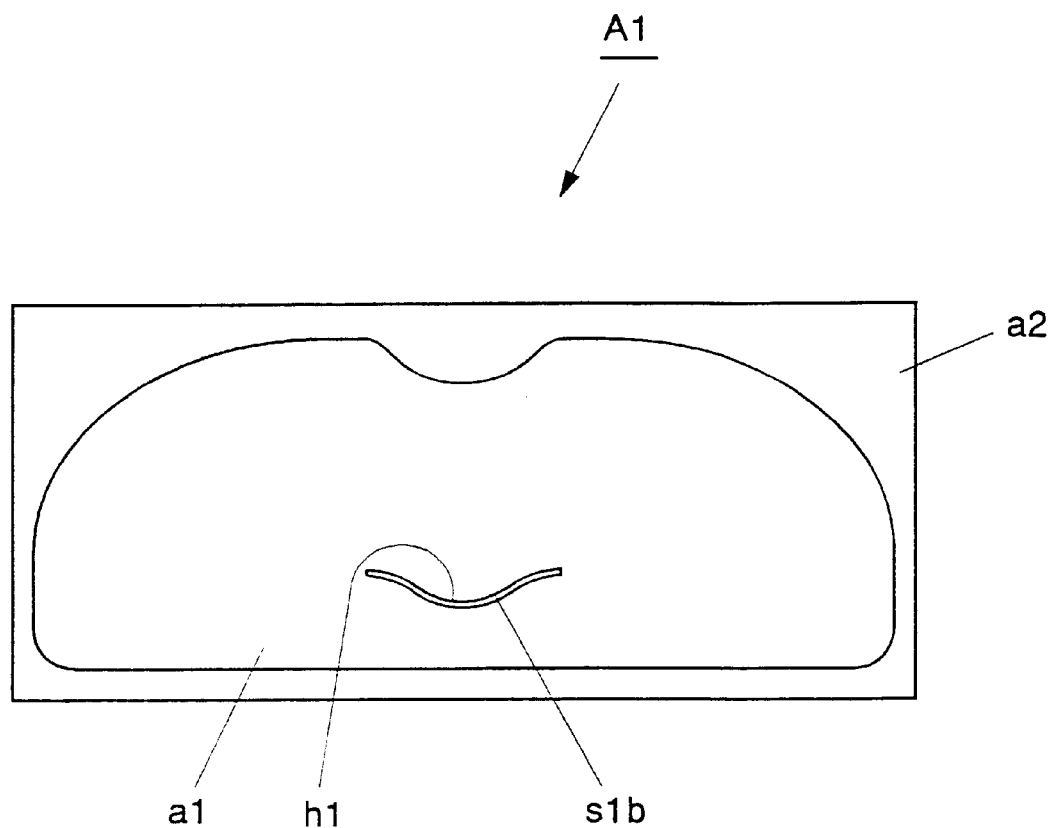
FIG. 3 is a plan view illustrating another example of the nose pack according to the present invention.

The slit may otherwise be in the form of a broken line (s1a) capable of forming a desired opening as shown in FIG. 2, or in, the form of a slot (s1b) with a small width formed by partially perforating the base sheet as shown in FIG. 3.

A cosmetic substance solution constituting the film-forming cosmetic substance in this example was prepared based on the formulation shown below.

| Ingredients (in 100 gram stock solution) | |
| --- | --- |
| Polyacrylic acid | 15% |
| Methyl paraben | 0.1% |
| Polyvinyl pyrrolidone | 3.0% |
| 70% Sorbitol solution | 5.0% |
| Glycerin | 5.0% |
| Titanium oxide | 5.0% |
| Polyoxyethylene sorbitan oleate [20E.O] | 20% |
| Purified water | suitable amount |
| Total | 100% |

Preparation

Film-forming components, i.e., polyacrylic acid and polyvinyl pyrrolidone were uniformly liquefied in an appropriate amount of purified water by the use of a stirrer. Then, titanium oxide, glycerin, sorbitol, polyoxyethylene sorbitan oleate [20E.O] and methyl paraben were added to the remaining purified water and sufficiently stirred. The resulting solution was added to the former liquid, followed. by further sufficiently stirring the resulting mixture liquid to give a uniform film-forming cosmetic substance.

The nose pack (A1) of the configuration thus described is advantageously used as follows.

Firstly, water or lotion is slightly and uniformly applied onto a portion of skin to which the nose pack is applied. Then, the nose pack is applied thereto so that the slit (s1) formed in the lower portion thereof is positioned at the apex portion of the nose. (Where the release layer is provided, it is removed prior to applying the nose pack to the nose.)

At that time, the nose pack (A1) curves along the shape of the nose, and the slit (s1) opens when a portion under the slit (s1) is pressed. The upper edge (h1) of the opening thus formed presents a convex shape for covering the apex portion of the nose.

Figure 4:
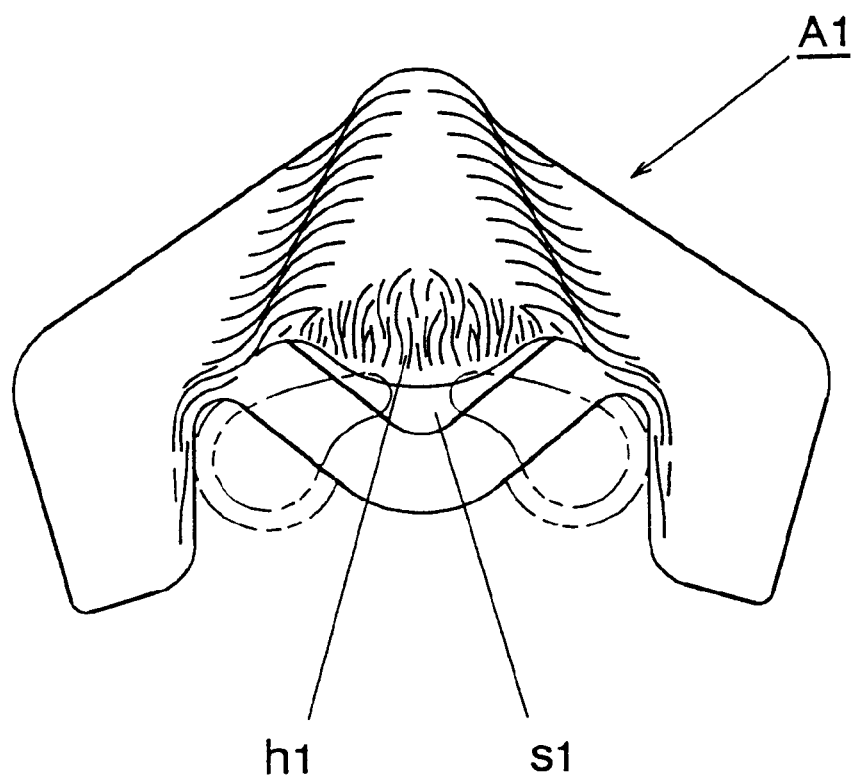
FIG. 4 is a perspective view of the nose pack shown in FIG. 1 as applied onto a nose and viewed from below.

Subsequently, when the upper edge (h1) of the opening is pressed onto the nose along the apex portion thereof, it curves as shown in FIG. 4 to closely fit the apex portion. Thus, the nose pack (A1) closely fits the whole nose including the dorsum portion, opposite ala portions and apex portion.

The film-forming cosmetic substance contained in end retained by the moisture-permeable base sheet is dissolved by the contacting water and hence contacts the skin. By virtue of quick humidity migration, the dissolved film-forming cosmetic substance quickly forms a film and, hence, a highly tough film is formed between the nose pack (A1) and the skin.

Accordingly, when the nose pack is peeled off by grasping one end of the moisture-permeable base sheet, the nose pack can be completely released without being broken or partially remaining on the skin due to the presence of the slit (s1) because the film thus formed has a sufficient film strength and is strongly integrated with the moisture-permeable base sheet to a certain depth. Thus, keratotic plugs, sebum, and dirt on the skin of the nose are removed as adhering to or captured by the film, whereby the whole area to which the pack is applied including the opposite ala portions, dorsum portion as well as apex portion of the nose can be sufficiently cared.

EXAMPLE 2

Figure 5:
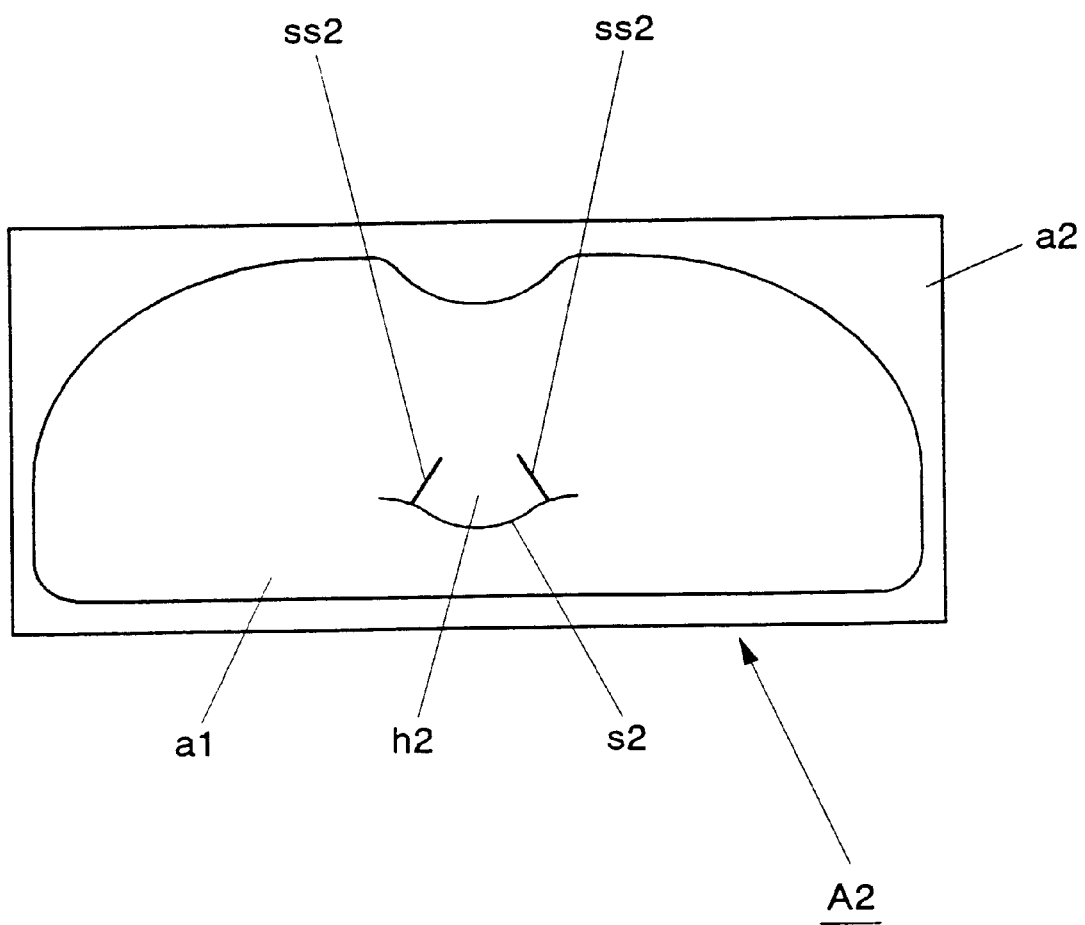
FIG. 5 is a plan view illustrating another example of the nose pack according to the present invention.

A nose pack (A2) is prepared in the same manner as in Example 1 except that slit (s2) formed in a lower portion of the moisture-permeable base sheet (a1) is formed with two sub-slits (ss2) (ss2) extending upward from upper edge (h2) thereof as shown in FIG. 5.

Although the slit (s2) in the nose pack (A2) shown is in the form of a continuous line, it may be in the form of a slot with a small width formed by partially perforating the base sheet or may be a broken line capable of forming a desired opening (not shown).

With the nose pack (A2) thus prepared, the provision of the sub-slits (ss2) enables the upper edge (h2) of the opening to be easily curved and further enlarges the area to be curved and, hence, the pack is possible to cover the apex portion of the nose as well as a middle portion of a nasal septum.

EXAMPLE 3

Figure 6:
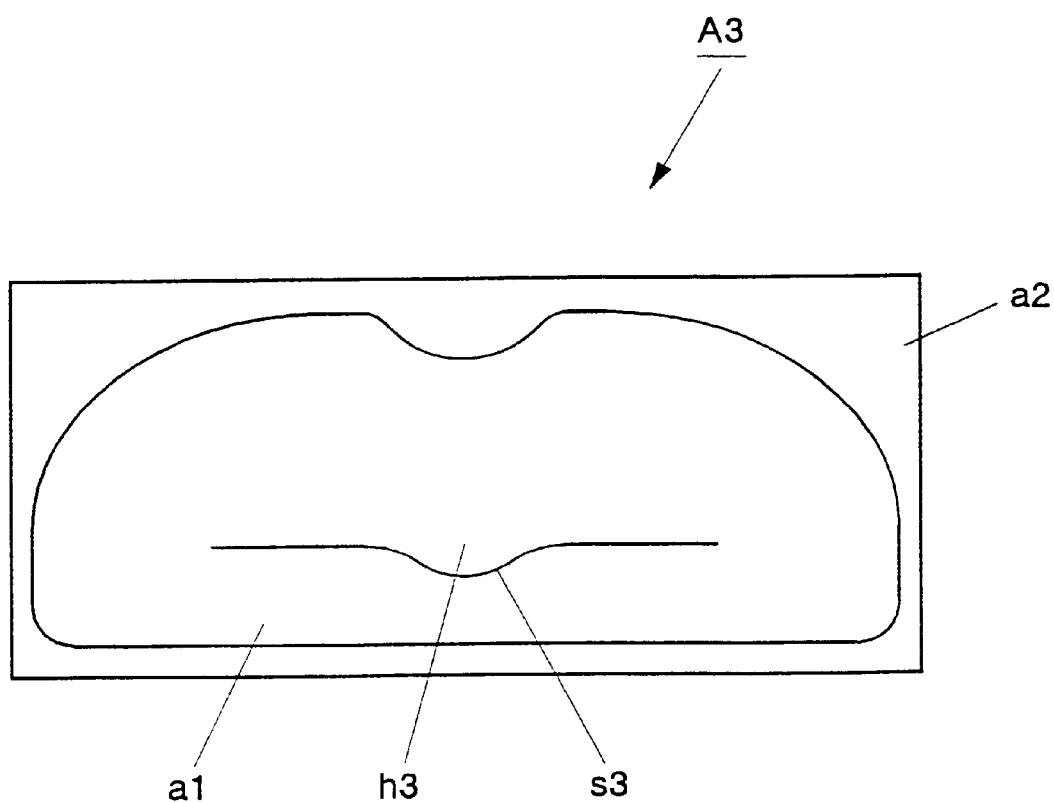
FIG. 6 is a plan view illustrating another example of the nose pack according to the present invention.

A nose pack (A3) is prepared in the same manner as in Example 1 except that the slit in the moisture-permeable base sheet is configured as shown in FIG. 6.

Specifically, slit (s3) of the nose pack (A3) is further extended laterally than Example 1.

Although the slit (s3) in the nose pack (A3) shown is in the form of a curved continuous line, it may be in the form of a broken line capable of forming a desired opening or in the form of a slot with a small width formed by partially perforating the base sheet (not shown).

Figure 7:
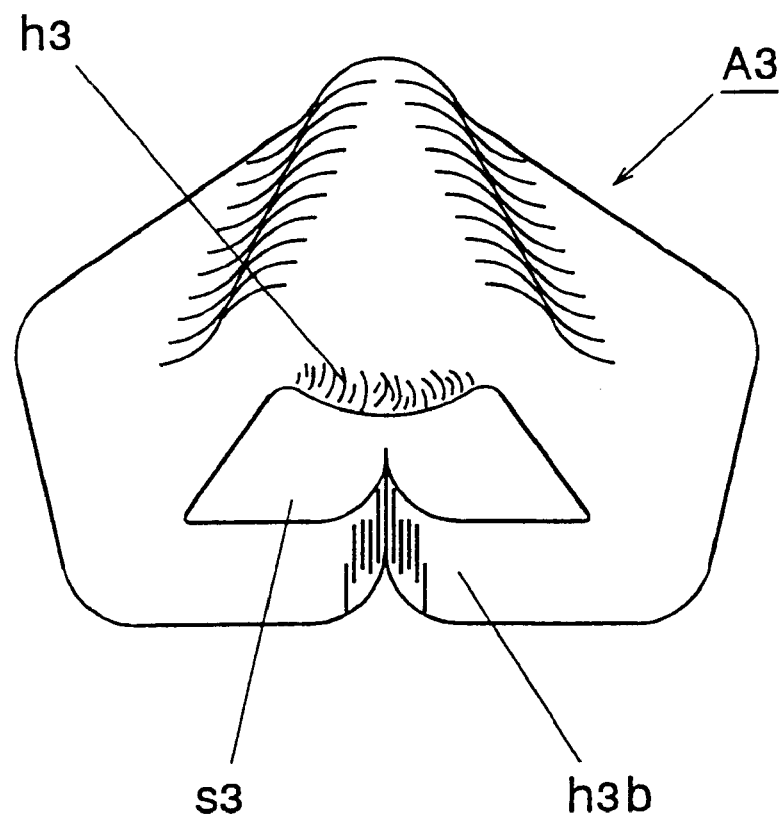
FIG. 7 is a perspective view of the nose pack shown in FIG. 6 as applied onto a nose and viewed from below.

In use, a portion of a nose to be applied with the nose pack (A3) is wetted with water in advance, and the nose pack is pressed thereonto. Subsequently, a lower edge (h3b) of an opening defined by the slit is pinched at the center thereof in such a manner as to fold the portion to bond the folded portion as shown in FIG. 7. As a result, the nose pack is entirely curved conformally to the shape of the nose with the slit (s3) being widely opened. At this time, upper edge (h3) of the opening becomes configured convex at the center thereof and linear at the opposite sides thereof.

Accordingly, when the upper edge (h3) of the opening is pressed onto the nose along the apex portion thereof, it is easily curved to sufficiently cover this portion. Thus, the nose pack (A3) closely fits the whole nose including the dorsum portion, opposite ala portions, and apex portion and, hence, the whole portion to which the pack is applied can be sufficiently cared.

Figure 8:
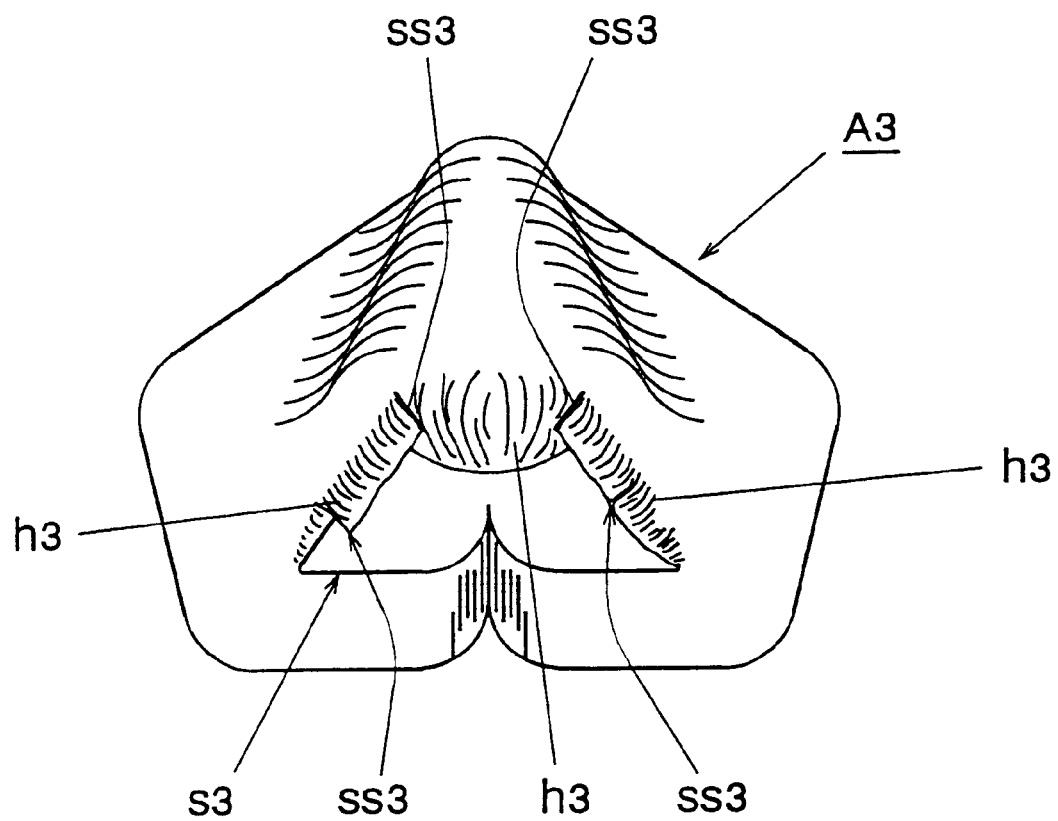
FIG. 8 is a perspective view illustrating another example of the nose pack according to the present invention as applied onto a nose and viewed from below.

It is to be noted that the provision of a plurality of sub-slits (ss3) extending from the slit (s3) as shown In FIG. 8 allows the substantially entire upper edge (h3) of the opening to be curved and hence makes it possible to cover the apex portion as well as the periphery of each nostril of the nose.

EXAMPLE 4

Figure 9:
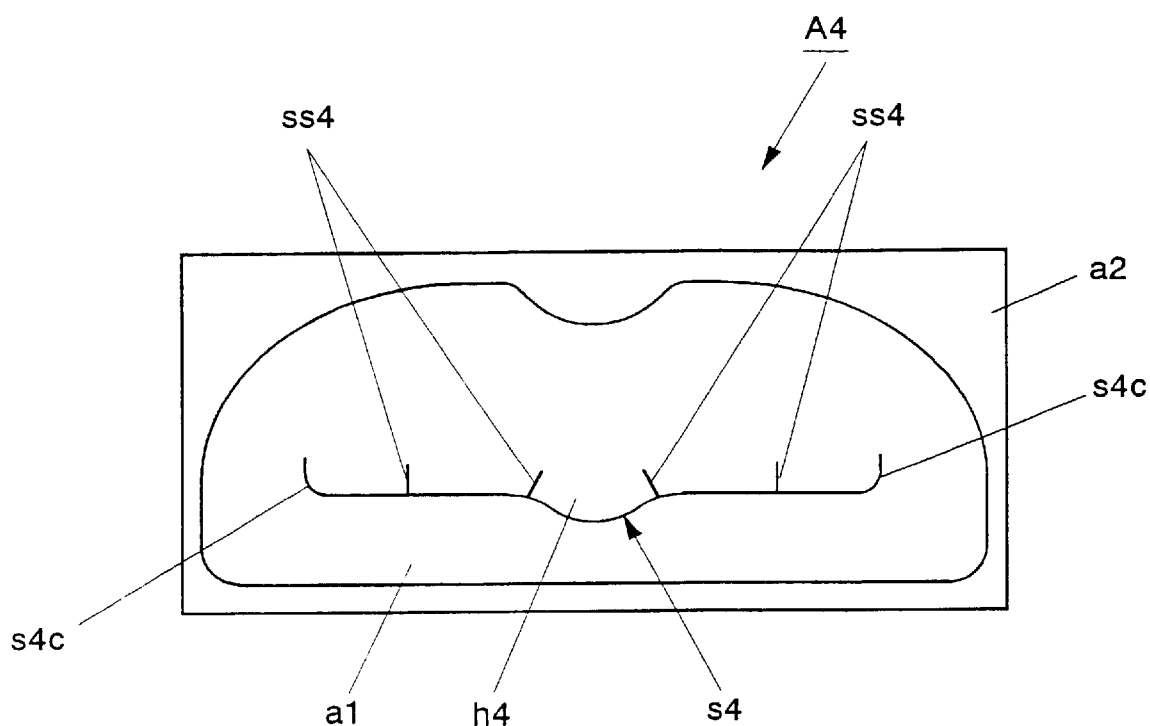
FIG. 9 is a plan view illustrating another example of the nose pack according to the present invention.

A nose pack (A4) is prepared in the same manner as in Example 3 except that the slit in the moisture-permeable base sheet is configured as shown in FIG. 9.

Specifically, slit (s4) of the nose pack (A4) is further extended than Example 3 to define opposite end portions (s4c) each corresponding to the outer edge of each ala portion of the nose.

A plurality of sub-slits (ss4) are optionally formed as extending from upper edge (h4) of an opening defined by the slit (s4) as shown.

Figure 10:
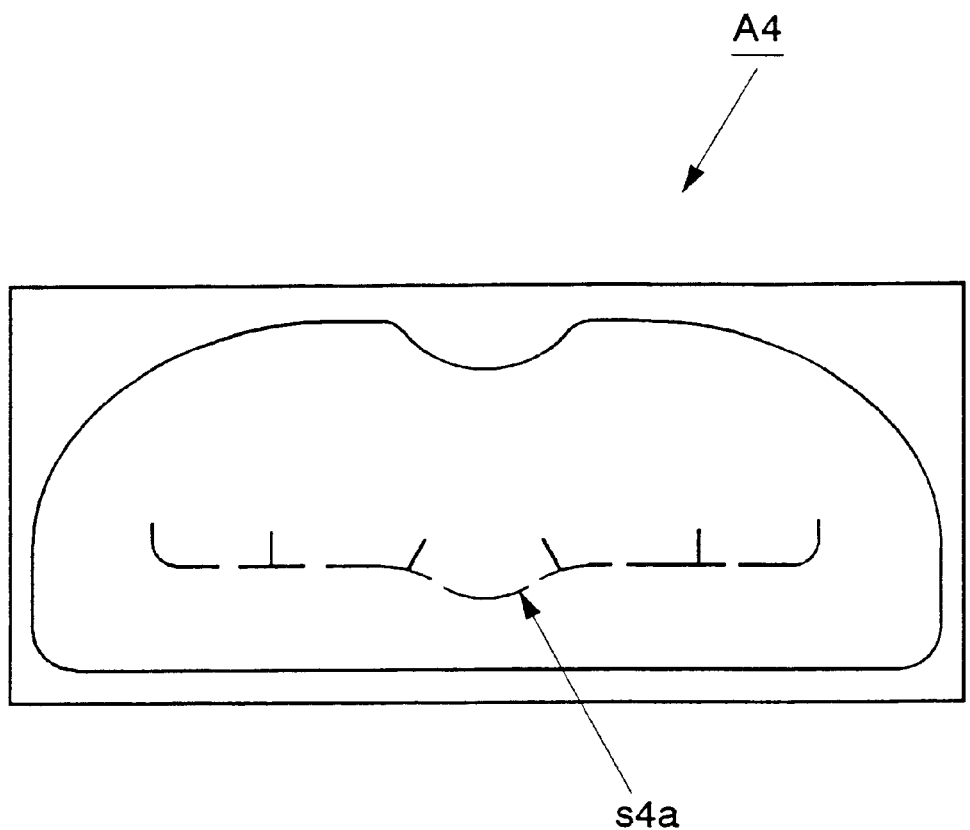
FIG. 10 is a plan view illustrating another example of the nose pack according to the present invention.
Figure 11:
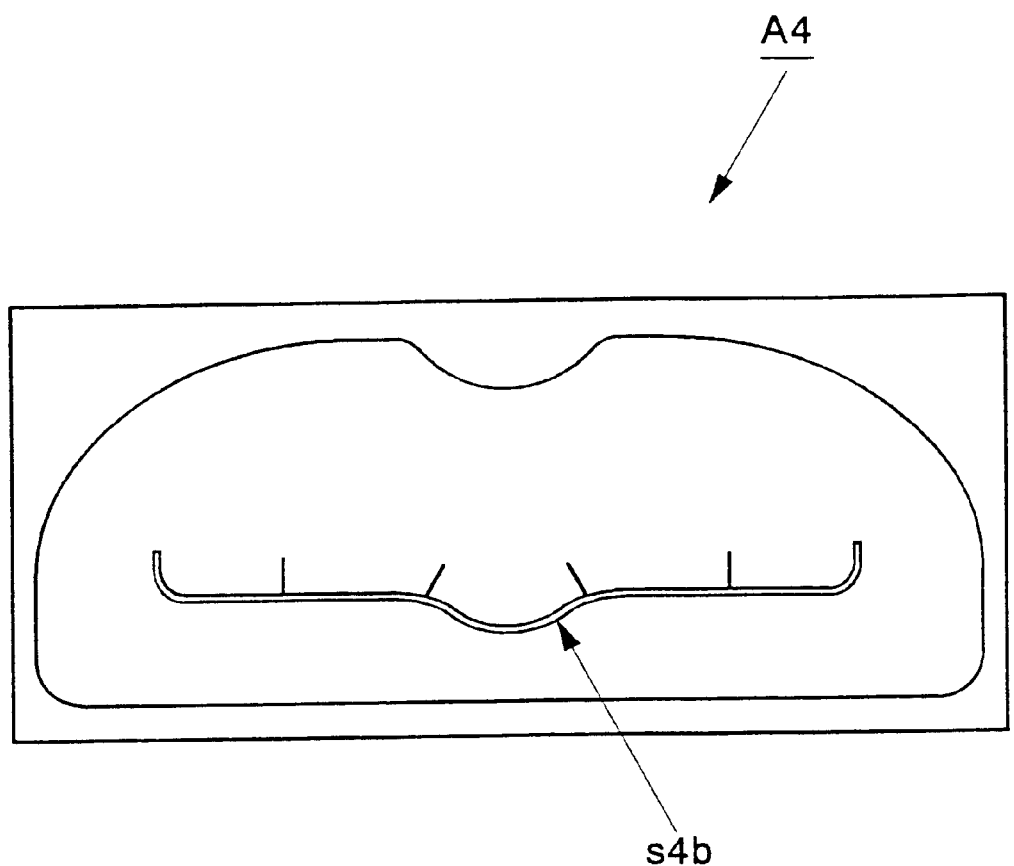
FIG. 11 is a plan view illustrating another example of the nose pack according to the present invention.

The slit (s4) may be in the form of a broken line (s4a) capable of forming a desired opening as shown in FIG. 10 or may be in the form of a slot (s4b) with a small width formed by partially perforating the base sheet as shown in FIG. 11.

Figure 12:
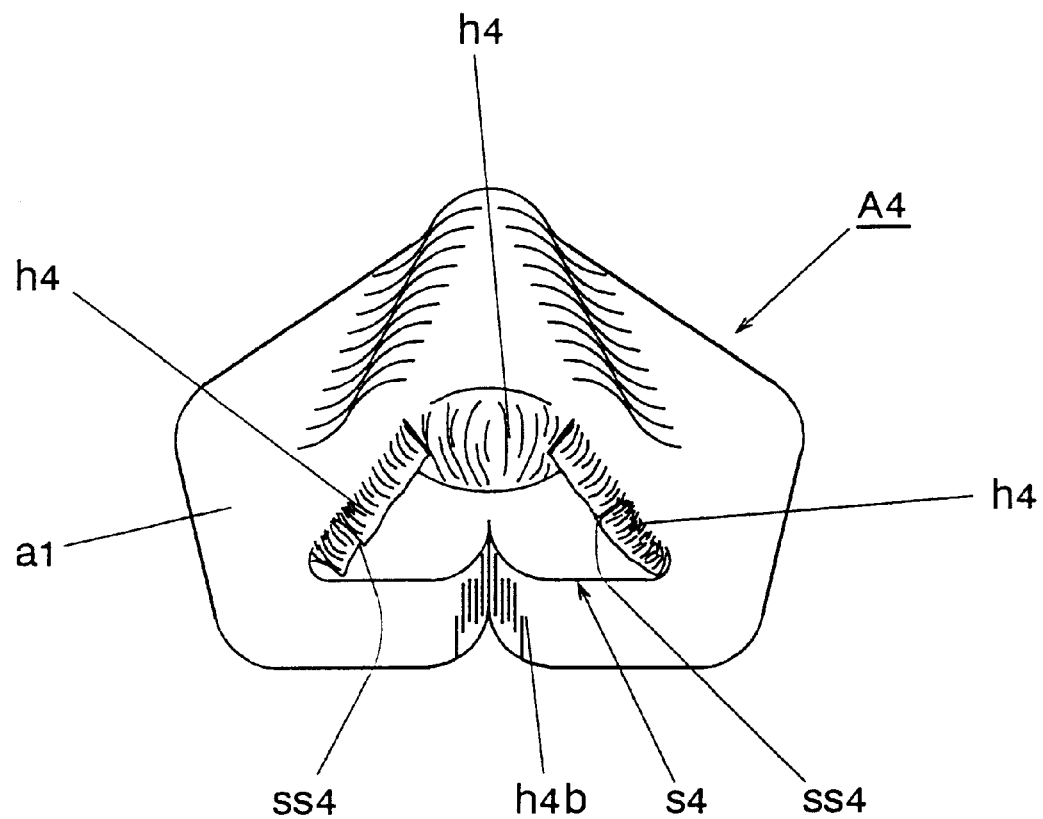
FIG. 12 is a perspective view of the nose pack shown in FIG. 9 as applied onto a nose and viewed from below.

In use, water or lotion is slightly and uniformly applied onto a nose with fingers, and at the same time, a lower edge portion (h4b) of the opening of the nose pack (A4) to be applied to the nose is also wetted with water or lotion. Then, the nose pack is pressed onto the nose and the lower edge (h4b) of the opening is pinched at the center thereof in such a manner as to fold the portion to bond the folded portion as shown in FIG. 12. As a result, the nose pack is entirely curved conformally to the shape of the nose with the slit (s4) being widely opened. At this time, the upper edge (h4) of the opening becomes configured convex at the center thereof, planar at the opposite sides thereof, and arcuated at the opposite ends thereof.

Accordingly, when the upper edge (h4) of the opening is pressed onto the nose along the apex portion of the nose and the periphery of each nostril, it is easily curved to sufficiently cover those portions while closely fitting each groove defined between the outer edge of each ala portion and the cheek.

Thus, the nose pack (A4) closely fits the whole nose including the dorsum portion, opposite ala portions, apex portion and periphery of-each nostril as well as the outer edge of each ala portion, and the groove defined between the outer edge of each ala portion and the cheek and, hence, than whole area to which the pack is applied can be sufficiently cared

EXAMPLE 5

Figure 13:
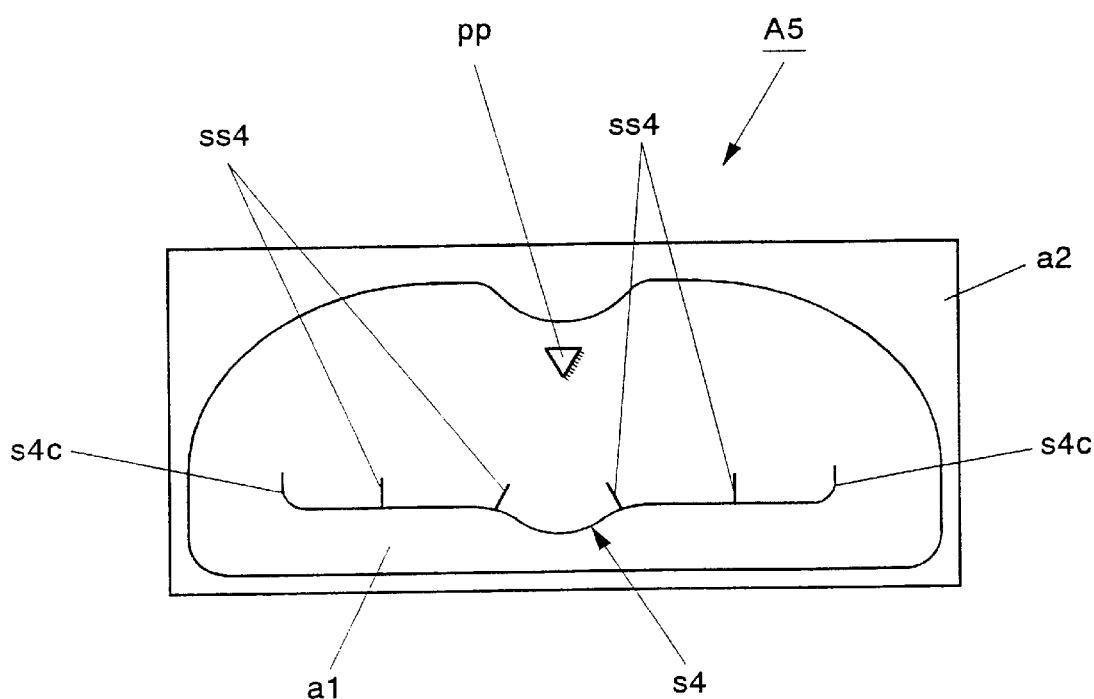
FIG. 13 is a plan view illustrating another example of the nose pack according to the present invention.

A nose pack (A5) is prepared in the same manner as in Example 4 except that a raised mark (pp) is formed at a center portion of the moisture-permeable base sheet using a press as shown in FIG. 13.

In addition to the same advantageous effects achieved by Example 4, this nose pack (A5) enables its easy positioning centrally of the nose by virtue of the mark (pp), and hence, the nose can be cared in a bilaterally balanced manner.

Instead of the raised mark, a depressed mark, a combined raised/depressed mark, a hole or a slit can be employed (not shown.)

EXAMPLE 6

Figure 14:
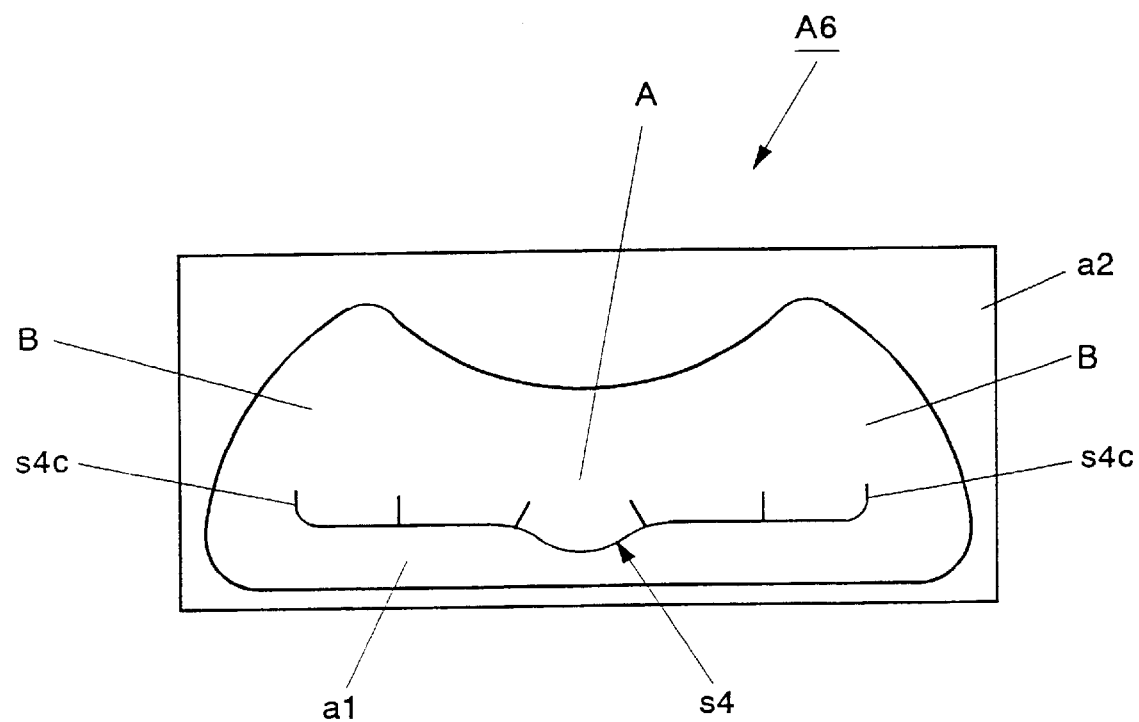
FIG. 14 is a plan view illustrating another example of the nose pack according to the present invention.
Figure 15:
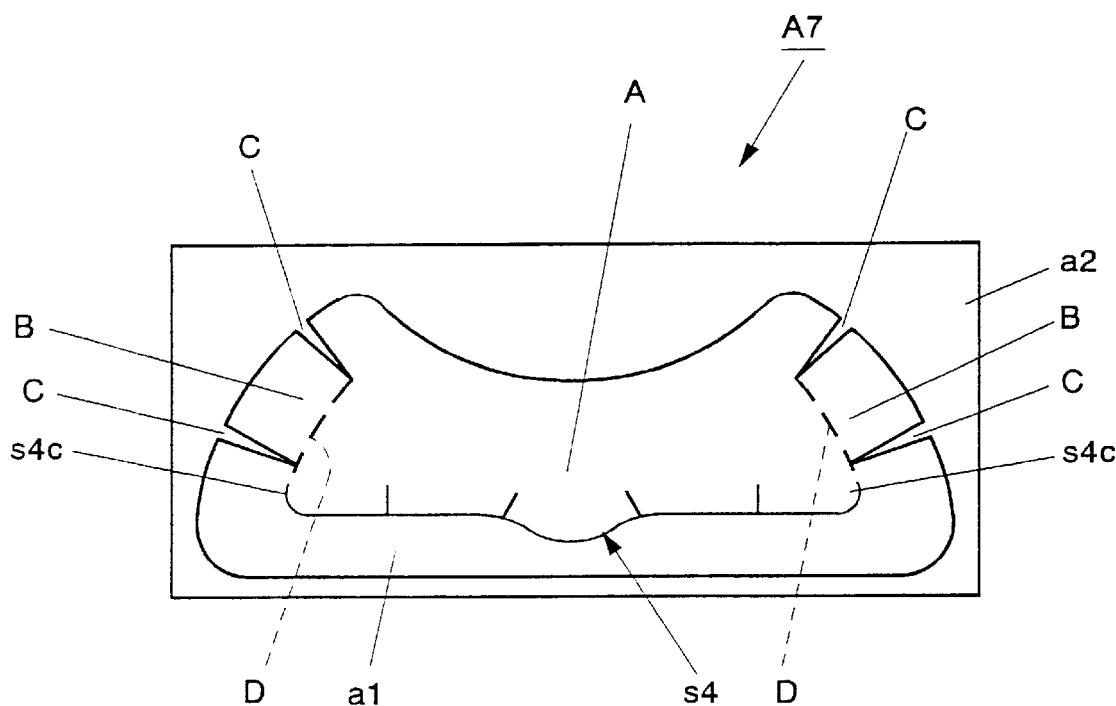
FIG. 15 is a plan view illustrating another example of the nose pack according to the present invention.

A nose pack (A6) is prepared in the same manner as in Example 4 except that it has a different outer form as shown in FIG. 14.

The moisture-permeable base sheet of the nose pack (A6) comprises a central narrow portion (A) defined between a centrally cut-away upper edge and a straight lower edge and a pair of largely arcuated portions (B) formed on opposite sides of the narrow portion. Accordingly, in addition to the same advantageous effects achieved by Example 4, the opposite ala portions can be sufficiently covered by the pack. This is because, in applying the pack onto the nose, the narrow portion (A) is positioned below the nasal bone so as to expose the root portion of the nose, while the largely arcuated portions (B) are positioned to cover the opposite ala portions sufficiently.

Further, each terminating portion (s4c) of slit (s4) enables the corresponding arcuated portion (B) to sufficiently cover and closely fit the groove defining the outer edge of the ala portion as well as a portion of the cheek, resulting in a sufficient care of these portions.

EXAMPLE 7

A nose pack (A7) is prepared In the same manner as in Example 6 except that notches (C) are provided at the lateral edge of each largely arcuated portion (B) as shown in FIG.

In addition to the same advantageous effects achieved by Example 6, this nose pack is capable of easily forming a crease (D) aligning with the groove defined between the outer edge of each ala portion and the cheek by virtue of the provision of the notches (C). This results in the nose pack capable of more closely fitting the groove and a portion of the cheek, thus enabling a sufficient care of these portion;

EXAMPLE 8

Figure 16:
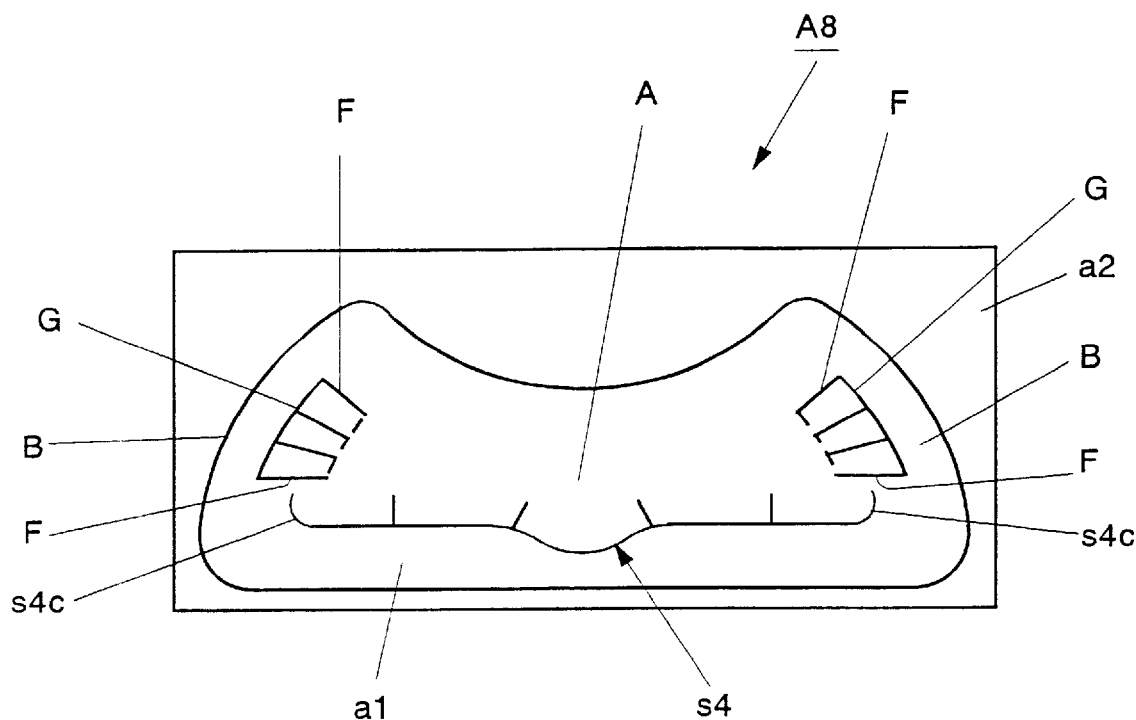
FIG. 16 is a plan view illustrating another example of the nose pack according to the present invention.

A nose pack (A8) is prepared in the same manner as in Example 6 except that each largely arcuated portion (B) is formed with a slit (G) extending substantially along the lateral edge thereof and slits (F) extending inwardly from the slit (G) as shown in FIG. 16.

These slits (F) and (G) allow the nose pack (A8) to be curved more conformally to each ala portion of a nose and hence to cover the entire ala portion. This enables the lateral edge portion of each arcuated portion (s) to easily fit the periphery of each ala portion

EXAMPLE 9

Figure 17:
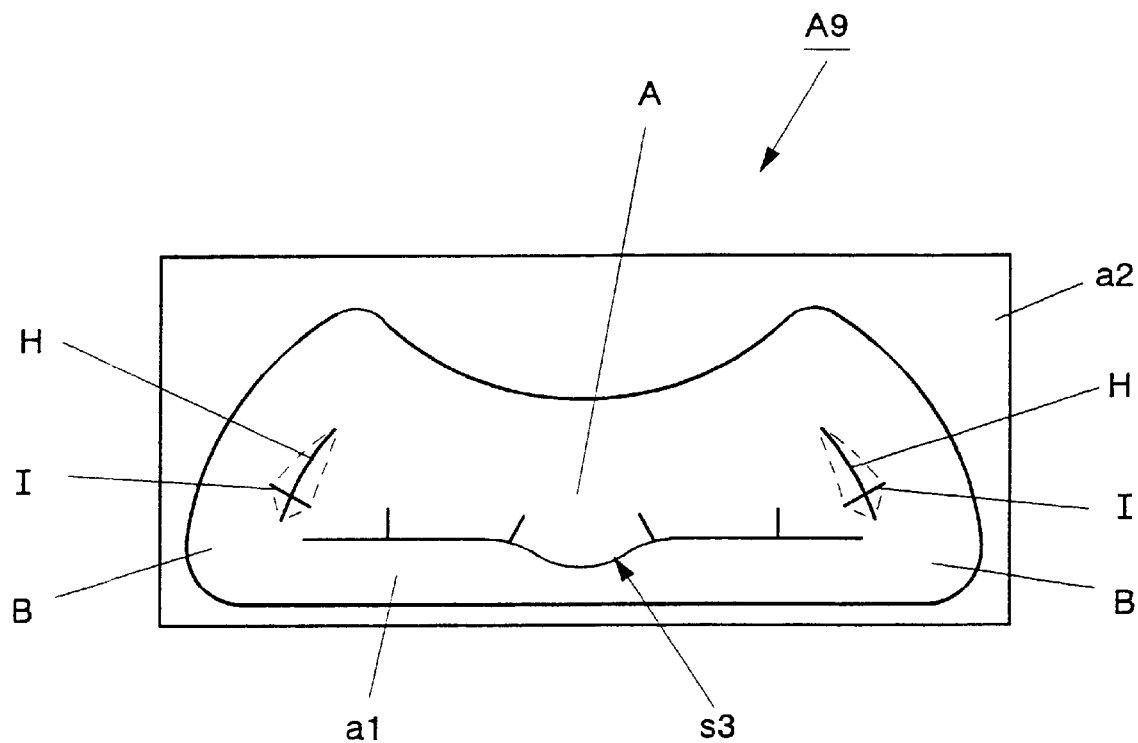
FIG. 17 is a plan view illustrating another example of the nose pack according to the present invention.

A nose pack (A9) is prepared in the same manner as in Example 6 except that slit (s3) provided in the moisture-permeable base sheet (a1) is substantially the same as that in Example 3 and each largely arcuated portion (B) is formed with a slit (H) extending generally along the lateral edge thereof and a slit (I) intersecting the slit (H) as shown in FIG. 17. These slits (H) and (I) allow the nose pack (A9) to be curved conformally to the bulge of each ala portion of a nose and hence to cover the entire ala portion thereby providing the same advantages as the nose pack of Example 5.

EXAMPLE 10

Another representative constitution of a nose pack in accordance with the present invention is the same as that of Examples 1 to 6 except that the film-forming cosmetic substance has the formulation shown below. The explanation of the constitution and advantages with reference to the drawings are omitted.

The cosmetic substance solution constituting the film-forming cosmetic substance in this example was prepared based on the formulation shown below.

| Ingredients (in 100 gram stock solution) | |
|---|---:|
| Polyacrylic acid | 10% |
| Pullulan | 5.0% |
| Methyl paraben | 0.1% |
| Polyvinyl pyrrolidone | 3.0% |
| 70% Sorbitol solution | 10.0% |
| Glycerin | 5.0% |
| Titanium oxide | 5.0% |
| Polyoxyethylene sorbitan oleate [20E.O] | 2.0% |
| Purified water | suitable amount |
| Total | 100% |

Preparation

Film-forming components, i.e., polyacrylic acid, pullulan and polyvinyl pyrrolidone were uniformly liquefied in an appropriate amount of purified water by the use of a stirrer. Then, titanium oxide, glycerin, sorbitol, polyoxyethylene sorbitan oleate [20E.O] and methyl paraben were added to the remaining purified water, and sufficiently stirred. The resulting solution was subsequently added to the former liquid, followed by further sufficiently stirring the resulting mixture liquid to give a uniform film-forming cosmetic substance.

Since the nose pack thus prepared contains polyacrylic acid and pullulan in the film-forming cosmetic substance, it has a strong adhesion to the skin and a high film strength and hence is capable of effectively removing keratotic plugs and sebum on the skin without being broken or partially remaining on the skin upon peeling off even if it is formed with a relatively large slit.

EXAMPLE 11

A nose pack is prepared in the same manner as in Example 1 except that the moisture-permeable base sheet is formed from a non-woven fabric comprising a fiber blend of rayon having a hydrophilic property and a polyester fiber material having a water-repellent property and an anchoring effect of about 10% by means of a certain surface active agent. The drawing of this example is omitted.

The moisture-permeable base sheet thus formed from such a fiber blend exhibits an increased anchoring effect with respect to a film-forming cosmetic substance compared with that formed of a polyester fiber material alone and, hence, breakage of the formed film upon peeling off can be prevented more effectively.

What is claimed is:

1. A nose pack comprising:
   a moisture-permeable base sheet, and a film-forming cosmetic substance contained in and carried by the base sheet;
   the base sheet having a slit in a lower portion of the base sheet for defining an opening in the base sheet such that an upper edge of the opening is applicable to at least an apex portion of a nose.

2. The nose pack according to claim 1, wherein the slit formed in the lower portion of the base sheet is capable of defining an opening such that an upper edge of the opening is applicable to at least the apex portion and adjacent periphery of nostrils of the nose.

3. The nose pack according to claim 1, wherein the slit formed in the lower portion of the base sheet is capable of defining an opening such that an upper edge of the opening is applicable to at least the apex portion, the adjacent periphery of the nostrils, and an outer edge of each ala portion of the nose.

4. The nose pack according to claim 1, wherein the slit is in the form of a single continuous line.

5. The nose pack according to claim 1, wherein at least this upper edge of the opening defined by the slit is provided with at least one sub-slit for facilitating curving of the base sheet.

6. The nose pack according to claim 1, wherein the moisture-permeable base sheet is provided with a vertically extending positioning slit in a center portion thereof between an upper edge of the base sheet and the slit formed in the lower portion of the base sheet.

7. The nose pack according to claim 1, wherein the moisture-permeable base sheet is provided with a positioning hole in a center portion thereof between an upper edge of the base sheet and the slit formed in the lower portion of the base sheet.

8. The nose pack according to claim 1, wherein the moisture-permeable base sheet has a center portion provided with a positioning mark comprising any one of a raised mark, a depressed mark and a combined raised/depressed mark.

9. The nose pack according to claim 1, wherein the moisture-permeable base sheet has a centrally cut-away upper edge and comprises a central narrow portion defined between the centrally cut-away upper edge and a lower edge of the base sheet and a pair of largely arcuated portions formed on opposite sides of the narrow portion, each having an area capable of covering each ala portion of-the nose, the centrally cut-away upper edge being such that when the nose pack is applied onto the nose, a root portion of the nose is exposed.

10. The nose pack according to claim 1, wherein the moisture-permeable base sheet is formed from a fiber bland of a hydrophilic fiber and a water-repellent fiber.

11. The nose pack according to claim 10, wherein the hydrophilic nature or the water repellency of at least one of the hydrophilic fiber and the water-repellent fiber is controlled by a surface-active agent.

12. The nose pack according to claim 1, wherein the film-forming cosmetic substance contains a film-forming cosmetic material mainly comprising polyacrylic acid.

13. The nose pack according to claim 12, wherein the polyacrylic acid is contained in the film-forming cosmetic substance in a dry amount of 1 to 98 wt. %.

14. The nose pack according to claim 1, wherein the film-forming cosmetic substance contains a film-forming cosmetic material mainly comprising polyacrylic acid and pullulan.

15. The nose pack according to claim 14, wherein the polyacrylic acid and pullulan are contained in the film-forming cosmetic substance in a total dry amount of 1 to 98 wt. %.

16. A nose pack comprising:
   a moisture-permeable base sheet, and a film-forming cosmetic substance contained in and carried by the base sheet;
   the base sheet having a slit in a lower portion thereof for defining an opening such that an upper edge of the opening is applicable to at least an apex portion of a nose, and wherein the slit is in the form of a broken line capable of defining the opening.

17. A nose pack comprising:
   a moisture-permeable base sheet, and a film-forming cosmetic substance contained in and carried by the base sheet;
   the base sheet having a slit in a lower portion thereof for defining an opening such that an upper edge of the opening is applicable to at least an apex portion of a nose, and wherein the slit is in the form of a perforated slot with a small width.

18. A nose pack comprising
   a moisture-permeable base sheet, and a film-forming cosmetic substance contained in and carried by the base sheet;
   the base sheet having a slit in a lower portion thereof for defining an opening such that an upper edge of the opening is applicable to at least an apex portion of a nose, wherein the moisture-permeable base sheet has a centrally cut-away upper edge and comprises a central narrow portion defined between the centrally cut-away upper edge and a lower edge of the base sheet and a pair of largely arcuated portions formed on opposite sides of the narrow portion, each having an area capable of covering each ala portion of the nose, the centrally cut-away upper edge being such that when the nose pack is applied onto the nose, a root portion of the nose is exposed, and wherein the largely arcuated portions each have a lateral edge portion formed with a plurality of small slits or notches extending inwardly from the lateral edge.

19. A nose pack comprising:

a moisture-permeable base sheet and a film-forming cosmetic substance contained in and carried by the base sheet;

the base sheet having a slit in a lower portion thereof for defining an opening such that an upper edge of the opening is applicable to at least an apex portion of a nose, wherein the moisture-permeable base sheet has a centrally cut-away upper edge and comprises a central narrow portion defined between the centrally cut-away upper edge and a lower edge of the base sheet and a pair of largely arcuated portions formed on opposite sides of the narrow portion, each having an area capable of covering each ala portion of the nose, the centrally cut-away upper edge being such that when the nose pack is applied onto the nose, a root portion of the nose is exposed, and wherein the largely arcuated portions each have a lateral edge adjacent which a slit for partially opening the nose pack is provided.

* * * * *